US008673274B2

(12) United States Patent
Schwartz et al.

(10) Patent No.: US 8,673,274 B2
(45) Date of Patent: *Mar. 18, 2014

(54) COMPOSITION COMPRISING PYRITHIONE OR A POLYVALENT METAL SALT OF A PYRITHIONE AND FURAMETPYR

(75) Inventors: James Robert Schwartz, West Chester, OH (US); David Joseph Kaufman, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 996 days.

This patent is subject to a terminal disclaimer.

(21) Appl. No.: 12/001,524

(22) Filed: Dec. 12, 2007

(65) Prior Publication Data

US 2008/0145328 A1 Jun. 19, 2008

Related U.S. Application Data

(60) Provisional application No. 60/875,230, filed on Dec. 15, 2006.

(51) Int. Cl.
*A01N 55/02* (2006.01)
*A01P 1/00* (2006.01)
*A01P 3/00* (2006.01)
*A61K 8/72* (2006.01)
*A61Q 5/00* (2006.01)

(52) U.S. Cl.
USPC ........................................ 424/70.11; 514/185

(58) Field of Classification Search
None
See application file for complete search history.

(56) References Cited

U.S. PATENT DOCUMENTS

| | | | |
|---|---|---|---|
| 2,396,278 A | 3/1946 | Lind | |
| 2,438,091 A | 3/1948 | Lynch et al. | |
| 2,486,921 A | 11/1949 | Byerly | |
| 2,486,922 A | 11/1949 | Strain | |
| 2,528,378 A | 10/1950 | Mannheimer | |
| 2,658,072 A | 11/1953 | Kosmin et al. | |
| 2,694,668 A | 11/1954 | Fricke | |
| 2,809,971 A | 10/1957 | Bernstein et al. | |
| 2,826,551 A | 3/1958 | Geen | |
| 3,152,046 A | 10/1964 | Ales | |
| 3,236,733 A | 2/1966 | Karstein et al. | |
| 3,332,880 A | 7/1967 | Kessler et al. | |
| 3,753,196 A | 8/1973 | Kurtz et al. | |
| 3,761,418 A | 9/1973 | Parran | |
| 3,929,678 A | 12/1975 | Laughlin et al. | |
| 3,958,581 A | 5/1976 | Abegg et al. | |
| 3,962,418 A | 6/1976 | Birkofer | |
| 3,964,500 A | 6/1976 | Drakoff | |
| 4,089,945 A | 5/1978 | Brinkman et al. | |
| 4,152,416 A | 5/1979 | Spitzer et al. | |
| 4,197,865 A | 4/1980 | Jacquet et al. | |
| 4,217,914 A | 8/1980 | Jacquet et al. | |
| 4,323,683 A | 4/1982 | Bolich, Jr. et al. | |
| 4,345,080 A | 8/1982 | Bolich, Jr. | |
| 4,364,837 A | 12/1982 | Pader | |
| 4,379,753 A | 4/1983 | Bolich, Jr. | |
| 4,381,919 A | 5/1983 | Jacquet et al. | |
| 4,422,853 A | 12/1983 | Jacquet et al. | |
| 4,470,982 A | 9/1984 | Winkler | |
| 4,507,280 A | 3/1985 | Pohl et al. | |
| 4,529,586 A | 7/1985 | De Marco et al. | |
| 4,663,158 A | 5/1987 | Wolfram et al. | |
| 4,877,441 A | 10/1989 | Mori et al. | |
| 4,885,107 A | 12/1989 | Wetzel | |
| 5,104,646 A | 4/1992 | Bolich, Jr. et al. | |
| 5,106,609 A | 4/1992 | Bolich, Jr. et al. | |
| RE34,584 E | 4/1994 | Grote et al. | |
| 5,518,744 A | 5/1996 | Kaeser et al. | |
| 5,674,478 A | 10/1997 | Dodd et al. | |
| 5,750,122 A | 5/1998 | Evans et al. | |
| 5,837,661 A | 11/1998 | Evans et al. | |
| 6,075,017 A * | 6/2000 | Dascalu et al. ............... | 514/188 |
| 6,531,496 B1 | 3/2003 | Uhr et al. | |
| 6,828,466 B2 | 12/2004 | Maleczka, Jr. et al. | |
| 7,026,308 B1 | 4/2006 | Gavin et al. | |
| 7,674,785 B2 | 3/2010 | Gavin et al. | |
| 7,867,361 B2 | 1/2011 | Salaam et al. | |
| 8,119,168 B2 | 2/2012 | Johnson et al. | |
| 8,491,877 B2 | 7/2013 | Schwartz et al. | |
| 2003/0223952 A1 | 12/2003 | Wells et al. | |
| 2004/0058855 A1 | 3/2004 | Schwartz et al. | |
| 2004/0191331 A1 | 9/2004 | Schwartz et al. | |
| 2004/0213751 A1 | 10/2004 | Schwartz et al. | |
| 2005/0202984 A1 | 9/2005 | Schwartz et al. | |
| 2006/0024381 A1* | 2/2006 | Schwartz et al. ............. | 424/641 |
| 2006/0076268 A1 | 4/2006 | Zare | |
| 2006/0086284 A1 | 4/2006 | Zhang et al. | |
| 2006/0210634 A1 | 9/2006 | Moerck et al. | |
| 2007/0092547 A1* | 4/2007 | Birnbaum et al. ............ | 424/405 |
| 2007/0128147 A1 | 6/2007 | Schwartz et al. | |
| 2008/0145328 A1 | 6/2008 | Schwartz | |
| 2008/0220103 A1 | 9/2008 | Birnbaum et al. | |
| 2008/0280929 A1 | 11/2008 | Cornish et al. | |

OTHER PUBLICATIONS

Nagahori et al., J. Agr. Food Chem., 2000, 48, 5760-5767.*
Nagahori et al. In Journal of Agriculture and Food Chemistry 2000, 48, 5754-5759.*
Nagahori et al. In Journal of Agriculture and Food Chemistry 2000, 48, 5760-5767.*
Talukdar, et al., *J. Colloid. Interfac. Sci.*, "Stochastic Reconstruction of Particulate Media from Two-Dimensional Images" 2002, 248, 429-42.
Gagnon, et al.,*J. Colloid. Interfac. Sci.*, "Comparison of the Structure and the Transport Properties of low-set and high-set Curdlan Hydrogels", 2011, 357, p. 419-427.
Eccleston, G. M., "Functions of Mixed Emulsifiers and Emulsifying Waxes in Dermatological Lotions and Creams," *Colloids and Surfaces A: Physiochem. And Eng. Aspects* 123-124 (1997) 169-182.
Eccleston, G. M., "The Microstructure of Semisolid Creams," *Pharmacy International*, vol. 7, 63-70 (1986).
*Encyclopedia of Polymer Science and Engineering*, "Silicones", vol. 15, 2d ed., pp. 204-308, John Wiley & Sons, Inc. (1989).
International Search Report, PCT/IB2007/0055095, dated Dec. 13, 2007.
Morioka, H., Tagaya, H., Karasu, M, Kadokawa, J, Chiba, K *Inorg. Chem.* "Effects of Zinc on the New Preparation Method of Hydroxy Double Salts" 1999, 38, 4211-6.

* cited by examiner

*Primary Examiner* — Dennis Heyer
(74) *Attorney, Agent, or Firm* — Linda M. Sivik

(57) ABSTRACT

The present invention relates to a composition comprising an effective amount of a pyrithione or a polyvalent metal salt of a pyrithione, an effective amount of furametpyr and an effective amount of a surfactant including a surfactant with an anionic functional group.

33 Claims, No Drawings

COMPOSITION COMPRISING PYRITHIONE OR A POLYVALENT METAL SALT OF A PYRITHIONE AND FURAMETPYR

CROSS REFERENCE TO RELATED APPLICATION

This application claims the benefit of U.S. Provisional Application No. 60/875,230, filed Dec. 15, 2006.

FIELD

The present invention relates to a composition comprising an effective amount of a pyrithione or a polyvalent metal salt of pyrithione, an effective amount of furametpyr, and an effective amount of a surfactant including a surfactant with an anionic functional group. More particularly, the present invention relates to personal care compositions and methods of treating microbial and fungal infections on the skin or scalp. Even more particularly, the present invention relates to methods for the treatment of dandruff and compositions, which provide improved anti-dandruff activity.

BACKGROUND

Anti-dandruff shampoos typically incorporate an anti-dandruff active and detergent surfactants. Among the type of anti-dandruff agents are particulate, crystalline anti-dandruff agents, such as sulfur, selenium sulfide and heavy metal salts of pyrithione. Soluble anti-dandruff agents, such as ketoconazole, are also commonly used.

Despite the options available, consumers still desire a shampoo that provides superior anti-dandruff efficacy versus currently marketed products; as such consumers have found that dandruff is still prevalent. Such a superior efficacy can be difficult to achieve.

Therefore, the use of other anti-fungal materials, such as furametpyr, in combination with pyrithione or a polyvalent metal salt of pyrithione or in combination with other antimicrobial agents, is desirable to increase the number of biological mechanisms simultaneously at work to control the relevant fungal population.

SUMMARY

An embodiment of the present invention is directed to composition comprising an effective amount of a pyrithione or a polyvalent metal salt of pyrithione, an effective amount of furametpyr, and an effective amount of a surfactant including a surfactant with an anionic functional group.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

It has now surprisingly been found, in accordance with the present invention, that anti-dandruff efficacy can be dramatically increased in topical compositions by the combination of an effective amount of a pyrithione or a polyvalent metal salt of pyrithione and furametpyr.

An embodiment of the present invention provides topical skin and/or hair compositions which provide superior benefits from a pyrithione or a polyvalent metal salt of pyrithione in combination with furametpyr. Therefore an embodiment of the present invention provides topical compositions with improved benefits to the skin and scalp (e.g., improved anti-dandruff efficacy). An embodiment of the present invention also provides a method for cleansing the hair and/or skin. These, and other benefits, will become readily apparent from the detailed description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

The components and/or steps, including those, which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more"

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

A. PYRITHIONE OR A POLYVALENT METAL SALT OF PYRITHIONE

In a preferred embodiment, the present may comprise pyrithione or a polyvalent metal salt of pyrithione. Any form of polyvalent metal pyrithione salts may be used, including platelet and needle structures. Preferred salts for use herein include those formed from the polyvalent metals magnesium, barium, bismuth, strontium, copper, zinc, cadmium, zirconium and mixtures thereof, more preferably zinc. Even more preferred for use herein is the zinc salt of 1-hydroxy-2-pyridinethione (known as "zinc pyrithione" or "ZPT"); more preferably ZPT in platelet particle form, wherein the particles have an average size of up to about 20 µm, preferably up to about 5 µm, more preferably up to about 2.5 µm.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

It is further contemplated that when ZPT is used as the anti-microbial particulate in the anti-microbial compositions herein, that an additional benefit of hair growth or re-growth may be stimulated or regulated, or both, or that hair loss may be reduced or inhibited, or that hair may appear thicker or fuller.

Zinc pyrithione may be made by reacting 1-hydroxy-2-pyridinethione (i.e., pyrithione acid) or a soluble salt thereof with a zinc salt (e.g. zinc sulfate) to form a zinc pyrithione precipitate, as illustrated in U.S. Pat. No. 2,809,971.

Preferred embodiments include from about 0.01% to about 5% of a pyrithione or polyvalent metal salt of a pyrithione; more preferably from about 0.1% to about 2%.

In embodiments having a particulate zinc material and a pyrithione or polyvalent metal salt of pyrithione, the ratio of particulate zinc material to pyrithione or a polyvalent metal salt of pyrithione is preferably from 5:100 to 10:1; more preferably from about 2:10 to 5:1; more preferably still from 1:2 to 3:1.

B. FURAMETPYR

In a preferred embodiment, the present invention may comprise furametpyr. Furametpyr is a fungicide, and more specifically, furametpyr is in the carboxamide class of anti-fungals. While not being bound by theory, it is generally thought that the furametpyr mechanism is the inhibition of mitochondrial succinate oxidation.

Preferred embodiments of the present invention include from about 0.01% to about 3% of a furametpyr; more preferably from about 0.1% to about 2%; more preferably still from about 0.2% to about 1.5%.

In the present invention, the combination of furametpyr with pyrithione or the polyvalent metal salts of pyrithione may result in an increase in efficacy of a composition. In an embodiment of the present invention, such an increase may be an increase in efficacy for anti-dandruff.

In a further embodiment of the present invention, furametpyr may also be used in combination with other anti-microbial agents. Non-limiting examples of other anti-microbial agents are ketoconazole, climbazole, octopirox, salicylic acid, coal tar, selenium sulfide and mixtures thereof. Such combinations of furametpyr with other anti-microbial agents, may result in an increase in efficacy of a composition, and even more particularly, may increase anti-dandruff efficacy.

Furametpyr generally comprises the following formula I:

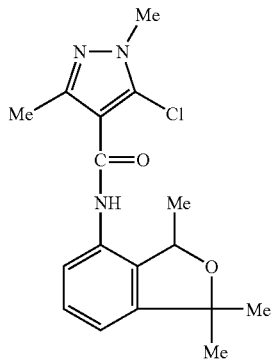 [SMILES: Cc1nn(C)c(Cl)c1C(=O)Nc1cccc2c1C(C)OC2(C)C]

Formula I

| Formula: | $C_{17}H_{20}ClN_3O_2$ |
| --- | --- |
| CAS/Registry Number: | 123572-88-3 |
| CA Index Name: | 1H-Pyrazole-4-carboxamide, 5-chloro-N-(1,3-dihydro-1,1,3-trimethyl-4-isobenzofuranyl)-1,3-dimethyl-(9CI) |
| Trade Names: | Limber ® |

C. PARTICULATE ZINC MATERIAL

In a further embodiment of the present invention, the composition of the present invention may include an effective amount of a particulate zinc material. Preferred embodiments of the present invention include from about 0.001% to about 10% of a particulate zinc layered material; more preferably from about 0.01% to about 7%; more preferably still from about 0.1% to about 5%.

Particulate zinc materials (PZM's) are zinc-containing materials which remain mostly insoluble within formulated compositions. Many benefits of PZM's require the zinc ion to be chemically available without being soluble, this is termed zinc lability. Physical properties of the particulate material have the potential to impact lability. We have discovered several factors which impact zinc lability and therefore have led to development of more effective formulas based on PZM's.

Particle physical properties which have been found to be important to optimize zinc lability of PZM's are morphology of the particle, surface area, crystallinity, bulk density, surface charge, refractive index, and purity level and mixtures thereof. Control of these physical properties has been shown to increase product performance.

Examples of particulate zinc materials useful in certain embodiments of the present invention include the following:

Inorganic Materials: Zinc aluminate, Zinc carbonate, Zinc oxide and materials containing zinc oxide (i.e., calamine), Zinc phosphates (i.e., orthophosphate and pyrophosphate), Zinc selenide, Zinc sulfide, Zinc silicates (i.e., ortho- and meta-zinc silicates), Zinc silicofluoride, Zinc Borate, Zinc hydroxide and hydroxy sulfate, zinc-containing layered materials and combinations thereof.

Further, layered structures are those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLM's) may have zinc incorporated in the layers and/or as more labile components of the gallery ions.

Many ZLM's occur naturally as minerals. Common examples include hydrozincite (zinc carbonate hydroxide), basic zinc carbonate, aurichalcite (zinc copper carbonate hydroxide), rosasite (copper zinc carbonate hydroxide) and many related minerals that are zinc-containing. Natural ZLM's can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLM's, which are often, but not always, synthetic, is layered doubly hydroxides, which are generally represented by the formula $[M^{2+}_{1-x}M^{+}_{x}(OH)_2]^{x+}$ $A^{m-}_{x/m} \cdot nH_2O$ and some or all of the divalent ions ($M^{2+}$) would be represented as zinc ions (Crepaldi, E L, Pava, P C, Tronto, J, Valim, J B *J. Colloid Interfac. Sci.* 2002, 248, 429-42).

Yet another class of ZLM's can be prepared called hydroxy double salts (Morioka, H., Tagaya, H., Karasu, M, Kadokawa, J, Chiba, K *Inorg. Chem.* 1999, 38, 4211-6). Hydroxy double salts can be represented by the general formula $[M^{2+}_{1-x}M^{2+}_{1+x}(OH)_{3(1-y)}]^{+} A^{n-}_{(1=3y)/n} \cdot nH_2O$ where the two metal ion may be different; if they are the same and represented by zinc, the formula simplifies to $[Zn_{1+x}(OH)_2]^{2x+}2xA^{-} \cdot nH_2O$. This latter formula represents (where x=0.4) common materials such as zinc hydroxychloride and zinc hydroxynitrate. These are related to hydrozincite as well wherein the divalent anion is replaced by a monovalent anion. These materials can also be formed in situ in a composition or in or during a production process.

These classes of ZLM's represent relatively common examples of the general category and are not intended to be limiting as to the broader scope of materials which fit this definition.

Natural Zinc containing materials/Ores and Minerals. Sphalerite (zinc blende), Wurtzite, Smithsonite, Franklinite, Zincite, Willemite, Troostite, Hemimorphite and combinations thereof.

Organic Salts. Zinc fatty acid salts (i.e., caproate, laurate, oleate, stearate, etc.), Zinc salts of alkyl sulfonic acids, Zinc naphthenate, Zinc tartrate, Zinc tannate, Zinc phytate, Zinc monoglycerolate, Zinc allantoinate, Zinc urate, Zinc amino acid salts (i.e., methionate, phenylalinate, tryptophanate, cysteinate, etc) and combinations thereof.

Polymeric Salts. Zinc polycarboxylates (i.e., polyacrylate), Zinc polysulfate and combinations thereof.

Physically Adsorbed Forms. Zinc-loaded ion exchange resins, Zinc adsorbed on particle surfaces, Composite particles in which zinc salts are incorporated, (i.e., as core/shell or aggregate morphologies) and combinations thereof.

Zinc Salts: zinc oxalate, zinc tannate, zinc tartrate, zinc citrate, zinc oxide, zinc carbonate, zinc hydroxide, zinc oleate, zinc phosphate, zinc silicate, zinc stearate, zinc sulfide, zinc undecylate, and the like, and mixtures thereof; preferably zinc oxide or zinc carbonate basic.

Commercially available sources of zinc oxide include Z-Cote and Z-Cote HPI (BASF), and USP I and USP II (Zinc Corporation of America).

Commercially available sources of zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA).

Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

Particle Size of PZM

In an embodiment of the present invention, it is has been found that a smaller particle size is inversely proportional to relative zinc lability D (90) is the particle size which corresponds to 90% of the amount of particles are below this size. In an embodiment of the present invention, the particulate zinc material may have a particle size distribution wherein 90% of the particles are less than about 50 microns. In a further embodiment of the present invention, the particulate zinc material may have a particle size distribution wherein 90% of the particles are less than about 30 microns. In yet a further embodiment of the present invention, the particulate zinc material may have a particle size distribution wherein 90% of the particles are less than about 20 microns.

Surface Area of PZM

In an embodiment of the present invention, there may be a direct relationship between surface area and relative zinc lability.

Increased particle surface area generally increases zinc lability due to kinetic factors. Particulate surface area can be increased by decreasing particle size and/or altering the particle morphology to result in a porous particle or one whose overall shape deviates geometrically from sphericity.

In an embodiment of the present invention, the basic zinc carbonate may have a surface area of greater than about 10 $m^2/gm$. In a further embodiment, the basic zinc carbonate may have a surface area of greater than about 20 $m^2/gm$. In yet a further embodiment of the present invention, the basic zinc carbonate may have a surface area of greater than about 30 $m^2/gm$.

In an embodiment of the present invention, it has further surprisingly been found, that anti-dandruff efficacy can further be increased in topical compositions by the combination of an effective amount of a pyrithione or a polyvalent metal salt of pyrithione and furametpyr, an effective amount of a particulate zinc material with a surfactant with an anionic functional group and wherein the particulate zinc material has a specified zinc lability within a surfactant system. Zinc lability is a measure of the chemical availability of zinc ion. Soluble zinc salts that do not complex with other species in solution have a relative zinc lability, by definition, of 100%. The use of partially soluble forms of zinc salts and/or incorporation in a matrix with potential complexants generally lowers the zinc lability substantially below the defined 100% maximum.

Labile zinc is maintained by choice of an effective particulate zinc material or formation of an effective particulate zinc material in-situ by known methods.

An embodiment of the present invention provides a stable composition for particulate zinc material dispersion where the zinc source resides in a particulate form. It has been shown to be challenging to formulate aqueous systems containing a particulate zinc material, due to the particulate zinc material's unique physical and chemical properties. Particulate zinc material may have a high density (approximately 3 $g/cm^3$), and needs to be evenly dispersed throughout the product and so it will not aggregate or settle. Particulate zinc material also has a very-reactive surface chemistry as well as the propensity to dissolve in systems with pH values below 6.5. Further, it has been surprisingly found in order for the particulate zinc material will remain as labile, in the presence of a surfactant with an anionic functional group.

A particulate zinc material with a solubility of less than 25% will have a measurable % soluble zinc value below a threshold value determined by the weight percent and molecular weight of the zinc compound. The theoretical threshold value can be calculated by the following equation:

$$\frac{0.25 * \text{wt. \% Zn Compound in Composition} * \text{moles of Zinc in Compound} * 65.39 \, (\text{MW of Zn})}{\text{MW of Zn Compound}}$$

An embodiment of the present invention is directed to a composition comprising an effective amount of a pyrithione or a polyvalent metal salt of pyrithione in combination with furametpyr; an effective amount of a particulate zinc material having a aqueous solubility of less than about 25% by weight at 25° C.; an effective amount of a surfactant with an anionic functional group; and water; wherein the pH of the composition is greater than about 6.5.

Zinc Binding Materials

Materials which have a high affinity for zinc and have the tendency to result in the formation of insoluble complexes of zinc can foul the surface of particulate zinc materials (PZM's). By "fouling" it is meant the formation of an insoluble surface layer of the zinc binding material (ZBM) zinc salt which interferes with the kinetic lability of zinc from the base PZM material. The magnitude of negative effect of ZBM's is the product of the strength of association to zinc and the relative amount of the ZBM (relative to the PZM surface area). The PZM's can tolerate a portion of surface coverage without substantial inhibition of kinetic lability.

Those materials with high potential to bind to the PZM surface are ZBM's that form only sparingly soluble salts with zinc in water. "Sparingly soluble" refers to zinc salts with 1 gram (g)/100 g water solubility or less. These are the materials that form precipitated surface species on the PZM that interfere with zinc lability. A summary of the solubilities of common zinc salts and further disclosure of zinc binding material is found in U.S. application Ser. No. 11/216,520, filed Aug. 31, 2005 on pages 9-12 and incorporated by reference herein.

Many common raw materials may be sources for inadvertent ZBM's. In the case of fatty acids, for example, any material which originates from triglycerides or fatty acids will likely contain some level of fatty acid ZBM in the raw material as used. Surfactants derived directly from triglycerides or those derived from fatty alcohols which are themselves derived from triglycerides will contain varying levels of fatty acids. Other raw materials may contain relatively low levels of ZBM's that are added for a secondary benefit. For example, citric acid is commonly used for pH control during raw material manufacture. It is not always obvious to the end user of a raw material if such ZBM's are present; this information can be obtained from the manufacturer or analyzed directly.

Maximization of zinc lability from PZM's requires either complete avoidance of the presence of ZBM's or limiting the amount of the material to avoid complete coverage of the surface area of the PZM (i.e., saturation). An approximation of the amount of ZBM required to completely cover a PZM can be calculated based on effective surface area of the PZM and a knowledge of how tightly the ZBM can pack on the surface. The following example is illustrative of the process of approximating how much ZBM is certain to saturate and foul the entire PZM surface. It will be calculated for the general case in which a ZBM packs on the surface in a manner analogous to a surfactant adsorbing at an oil-water interface. In this case, a common value for surface area occupied per molecule is 30 Å$^2$ (equivalent to $3 \times 10^{-7} \mu^2$). It will be calculated per gram of a PZM with a measured surface area (SA, in m 2/g):

$$\frac{1 \, m^2 ZBM}{g \, PZM \cdot SA \, PZM} \times \frac{ZBM \, molecule}{3 \times 10^{-7} \mu^2 \, ZBM} \times \left(\frac{1 \times 10^6 \mu ZBM}{m \, ZBM}\right)^2 \times$$

$$\frac{mol \, ZBM}{6.02 \times 10^{23} \, molecules \, ZBM} \times \frac{1 \times 10^6 \, \mu mol \, ZBM}{mol \, ZBM} =$$

$$5.5 \, \mu mol \, ZBM/g \, PZM\text{-}SA \, PZM$$

Thus, 5.5 micromoles of ZBM will saturate 1 g of a PZM with a surface area of 1 m$^2$/g. Therefore, for the present invention, it is desirable that the composition comprises less than 5.5 micromoles of a zinc binding material (ZBM) per gram (g) of a particulate zinc material (PZM)/per m$^2$/g surface area of a particulate zinc material (PZM).

For an example of zinc carbonate (a PZM) with a surface area of 30 m$^2$/g and laurate as the ZBM, the calculation then becomes:

$$\frac{30 \, m^2 ZC}{g \, ZC} \times \left(\frac{1 \times 10^6 \, \mu ZC}{m \, ZC}\right)^2 \times \frac{LA \, molecule}{3 \times 10^{-7} \mu^2} \times$$

$$\frac{mole \, LA}{6.02 \times 10^{23} \, molecules \, LA} \times \frac{200 \, g \, LA}{mole \, LA} = 0.03 \, g \, LA/g \, ZC$$

Thus, approximately 0.03 g of laurate would saturate and foul the surface of one gram of a zinc carbonate PZM with the specified surface area. Based on this type of analysis, other "fouling levels" can be established for the specific ZBM-PZM combination. However, this example provides an approximation of the range of levels that need to be controlled to assure zinc lability of the PZM.

More specifically, then, a formulation containing 1.6% of the zinc carbonate specified above would require a laurate level below 0.048% (480 ppm) to remain effective. This would represent the total laurate present, whether added directly or inadvertently entering a formula via other raw material additions. This level also assumes there are no other ZBM's present; if there are, each needs to be considered separately while maintaining a combined amount below surface saturation level.

D. TOPICAL CARRIER

In a preferred embodiment, the composition of the present invention is in the form of a topical composition, which includes a topical carrier. Preferably, the topical carrier is selected from a broad range of traditional personal care carriers depending on the type of composition to be formed. By suitable selections of compatible carriers, it is contemplated that such a composition is prepared in the form of daily skin or hair products including conditioning treatments, cleansing products, such as hair and/or scalp shampoos, body washes, hand cleansers, water-less hand sanitizer/cleansers, facial cleansers and the like.

In a preferred embodiment, the carrier is water. Preferably the compositions of the present invention comprise from 40% to 95% water by weight of the composition; preferably from 50% to 85%, more preferably still from 60% to 80%.

E. DETERSIVE SURFACTANT

The composition of the present invention includes a detersive surfactant. The detersive surfactant component is included to provide cleaning performance to the composition. The detersive surfactant component in turn comprises anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the composition herein include those which are known for use in hair care or other personal care cleansing compositions. The concentration of the anionic surfactant component in the composition should be sufficient to provide the desired cleaning and lather performance, and generally range from about 2% to about 50%, preferably from about 8% to about 30%, more preferably from about 10% to about 25%, even more preferably from about 12% to about 22%.

Preferred anionic surfactants suitable for use in the compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $[R^1—SO_3\text{-}M]$ where $R^1$ is a straight or branched chain, saturated, aliphatic hydrocarbon radical having from about 8 to about 24, preferably about 10 to about 18, carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinates, examples of which include disodium N-octadecylsulfosuccinate; disodium lauryl sulfosuccinate; diammonium lauryl; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic detersive surfactants suitable for use in the compositions are the beta-alkyloxy alkane sulfonates. These surfactants conform to the formula

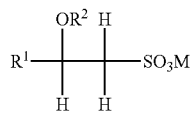

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment of the present invention, the anionic surfactant is preferably sodium lauryl sulfate or sodium laureth sulfate.

Suitable amphoteric or zwitterionic detersive surfactants for use in the composition herein include those which are known for use in hair care or other personal care cleansing. Concentration of such amphoteric detersive surfactants preferably ranges from about 0.5% to about 20%, preferably from about 1% to about 10%. Non limiting examples of suitable zwitterionic or amphoteric surfactants are described in U.S. Pat. Nos. 5,104,646 (Bolich Jr. et al.), 5,106,609 (Bolich Jr. et al.).

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the composition are well known in the art, and include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

F. DISPERSED PARTICLES

The composition of the present invention may include dispersed particles. In the compositions of the present invention, it is preferable to incorporate at least 0.025% by weight of the dispersed particles, more preferably at least 0.05%, still more preferably at least 0.1%, even more preferably at least 0.25%, and yet more preferably at least 0.5% by weight of the dispersed particles. In the compositions of the present invention, it is preferable to incorporate no more than about 20% by weight of the dispersed particles, more preferably no more than about 10%, still more preferably no more than 5%, even more preferably no more than 3%, and yet more preferably no more than 2% by weight of the dispersed particles.

G. DISPERSED GEL NETWORK PHASE

In an embodiment of the present invention, the shampoo compositions of the present invention may comprise a dispersed gel network phase comprising a fatty amphiphile. The gel network phase may be included in shampoo compositions of the present invention to provide conditioning benefits. As used herein, the term "gel network" refers to a lamellar or vesicular solid crystalline phase which comprises at least one fatty amphiphile as specified below, at least one secondary surfactant as specified below, and water or other suitable solvents. The lamellar or vesicular phase comprises bi-layers made up of a first layer comprising the fatty amphiphile and the secondary surfactant and alternating with a second layer comprising the water or other suitable solvent. The term "solid crystalline", as used herein, refers to the structure of the lamellar or vesicular phase which forms at a temperature below the chain melt temperature of the layer in the gel network comprising the one or more fatty amphiphiles, the chain melt temperature being at least about 27° C. The chain melt temperature may be measured by differential scanning calorimetry, a method of which is described in the Examples below.

Gel networks which comprise, for example, fatty alcohols have been used for years in cosmetic creams and hair conditioners. Such cosmetic creams and hair conditioners, however, typically contain very low amounts, if any, of detersive surfactant. Thus, such known products do not provide a combination of cleansing and conditioning to the hair or skin.

Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International, Vol.* 7, 63-70 (1986).

In a further embodiment of the present invention, the dispersed gel network phase is pre-formed. The term "pre-formed", as used herein, means that the mixture of the fatty amphiphile, secondary surfactant, and water or other suitable solvent is substantially a solid crystalline phase when added to the other components of the shampoo composition.

According to this embodiment of the present invention, the gel network component of the present invention is prepared as a separate pre-mix, which, after being cooled, is subsequently incorporated with the detersive surfactant and the other components of the shampoo composition. More specifically, the gel network component of the present invention may be prepared by heating the fatty amphiphile, the secondary surfactant, and water to a level in the range of about 75° C. to about 90° C. and mixing. This mixture is cooled to a level in the range of about 27° C. to about 35° C. by, for example, passing the mixture through a heat exchanger. As a result of this cooling step, the fatty amphiphile and the secondary surfactant crystallize to form a solid crystalline gel network.

As used herein, "fatty amphiphile" refers to a compound having a hydrophobic tail group of $R_1$ as defined below and a hydrophilic head group which does not make the compound water soluble, wherein the compound also has a net neutral charge at the pH of the shampoo composition. The term "water soluble", as used herein, means that the material is soluble in water in the present composition. As used herein, "secondary surfactant" refers to one or more surfactants which are combined with the fatty amphiphile and water to form the gel network of the present invention as a pre-mix separate from the other components of the shampoo composition. The secondary surfactant is separate from and in addition to the detersive surfactant component of the shampoo composition. However, the secondary surfactant may be the same or different type of surfactant or surfactants as that or those selected for the detersive surfactant component described herein. As used herein, the term "suitable solvent" refers to any solvent which can be used in the place of or in combination with water in the formation of the gel network of the present invention.

In a further embodiment of the present invention, a composition may comprise an effective amount of a pyrithione or a polyvalent metal salt of a pyrithione or other anti-microbial active; furametpyr, an effective amount of a surfactant including a detersive surfactant with an anionic functional group, and a dispersed gel network phase comprising: i) at least about 0.05% of one or more fatty amphiphiles, by weight of said shampoo composition; ii) at least about 0.01% of one or more secondary surfactants, by weight of said shampoo composition; and iii) water; and at least about 20% of an aqueous carrier, by weight of said shampoo composition. In yet a further embodiment, the composition above may further comprise an effective amount of a particulate zinc material.

U.S. patent application Ser. No. 11/228,770, filed on Sep. 16, 2005 comprises further details on Dispersed Gel Networks, fatty amphiphiles, secondary surfactant, and water or suitable solvent, as described herein and is incorporated by reference herein.

H. AQUEOUS CARRIER

The compositions of the present invention are typically in the form of pourable liquids (under ambient conditions). The compositions will therefore typically comprise an aqueous carrier, which is present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

I. ADDITIONAL COMPONENTS

The compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10%.

Non-limiting examples of optional components for use in the composition include cationic polymers, conditioning agents (hydrocarbon oils, fatty esters, silicones), anti dandruff agents, suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins, minerals, herbal/fruit/food extracts, sphingolipids derivatives or synthetical derivative, and clay.

1. Cationic Polymers

The compositions of the present invention may contain a cationic polymer. Concentrations of the cationic polymer in the composition typically range from about 0.05% to about 3%, preferably from about 0.075% to about 2.0%, more preferably from about 0.1% to about 1.0%. Preferred cationic polymers will have cationic charge densities of at least about 0.4 meq/gm, preferably at least about 1.2 meq/gm, more preferably at least about 1.5 meq/gm, but also preferably less than about 7 meq/gm, more preferably less than about 5 meq/gm. Herein, "cationic charge density" of a polymer refers to the ratio of the number of positive charges on the polymer to the molecular weight of the polymer. The average molecular weight of such suitable cationic polymers will generally be between about 10,000 and 10 million, preferably between about 50,000 and about 5 million, more preferably between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. These preferred monomers conform the to the formula

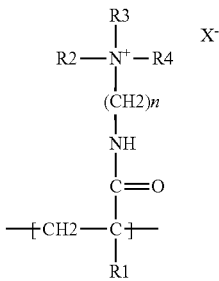

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the formula

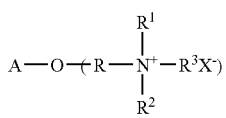

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

A potential side reaction that may occur during the quaternization reaction of a cationic polymer production process is the formation of trimethylamine (TMA). While not intending to be limited by theory, the presence of TMA as an impurity in a cationic polymer containing composition at a pH greater than 6.8 may be found to be the source of an amine off-odor or fishy off-odor. It has surprisingly been discovered that pH has a significant effect on the level of TMA evolved into the headspace of the composition—in particular, the level of TMA in the headspace increases as the pH increases. Headspace is commonly referred to as the volume above a liquid or solid in a closed container. In turn, the level of amine off-odor can be found to be proportional to the level of TMA present in the headspace. Additionally, it has been discovered that it is possible to reverse the TMA evolution into the headspace by lowering the pH of the composition, as demonstrated and discussed in U.S. application Ser. No. 11/216,520, filed Aug. 31, 2005 on pages 22-26 and incorporated by reference herein.

Therefore, in order to produce an acceptable composition having a pH of greater than 6.8, which comprises a cationic polymer, with low to no amine off-odor, it has been discovered that it may be necessary to use a cationic polymer which contains from no detectable TMA to low levels of TMA. Levels of TMA from a cationic polymer can be measured using the method as demonstrated and discussed in U.S. application Ser. No. 11/216,520, filed Aug. 31, 2005 on pages 22-26 and incorporated by reference herein.

It has been discovered that compositions comprising cationic polymers which have levels of TMA, as measured, for example, in the method described above, below 45 ppm, preferably below 25 ppm, more preferably below 17 ppm, have no amine off-odor to low amine off-odor which has been found to be acceptable.

Odor Evaluations

Expert olfactory panelists may be used to judge odor on any convenient scale. For example, a scale of 0 (no detectable amine off-odor) to 10 (high amine off-odor) can be established and used for grading purposes. The establishment of such tests is a matter of routine, and various other protocols can be devised according to the desires of an individual.

2. Nonionic Polymers

Polyalkylene glycols having a molecular weight of more than about 1000 are useful herein. Useful are those having the following general formula:

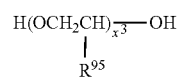

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

3. Conditioning Agents

Conditioning agents include any material which is used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The conditioning agents useful in the compositions of the present invention typically comprise a water insoluble, water dispersible, nonvolatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, more preferably from about 100,000 to about 1,500,000 csk.

The dispersed silicone conditioning agent particles typically have a volume average particle diameter ranging from about 0.01 µm to about 50 µm, as measured using the Horiba LA-910 Particle Size Analyzer. The Horiba LA-910 instrument uses the principles of low-angle Fraunhofer Diffraction and Light Scattering to measure the particle size and distribution in a dilute solution of particles. For small particle application to hair, the volume average particle diameters typically range from about 0.01 µm to about 4 µm, preferably from about 0.01 µm to about 2 µm, more preferably from about 0.01 µm to about 0.5 µm. For larger particle application to hair, the volume average particle diameters typically range from about 4 µm to about 50 µm, preferably from about 6 µm to about 40 µm, and more preferably from about 10 µm to about 35 µm.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

a. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (III):

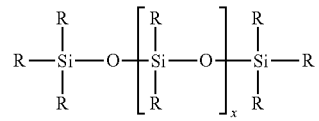

wherein R is aliphatic, preferably alkyl or alkenyl, or aryl, R can be substituted or unsubstituted, and x is an integer from 1 to about 8,000. Suitable R groups for use in the compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Preferred alkyl and alkenyl substituents are $C_1$ to $C_5$ alkyls and alkenyls, more preferably from $C_1$ to $C_4$, more preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, more preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described herein.

b. Amino and Cationic Silicones

Cationic silicone fluids suitable for use in the compositions of the present invention include, but are not limited to, those which conform to the general formula (V):

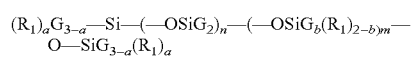

wherein G is hydrogen, phenyl, hydroxy, or $C_1$-$C_8$ alkyl, preferably methyl; a is 0 or an integer having a value from 1 to 3, preferably 0; b is 0 or 1, preferably 1; n is a number from 0 to 1,999, preferably from 49 to 499; m is an integer from 1 to 2,000, preferably from 1 to 10; the sum of n and m is a number from 1 to 2,000, preferably from 50 to 500; $R_1$ is a monovalent radical conforming to the general formula $CqH_{2q}L$, wherein q is an integer having a value from 2 to 8 and L is selected from the following groups:

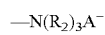

wherein $R_2$ is hydrogen, phenyl, benzyl, or a saturated hydrocarbon radical, preferably an alkyl radical from about $C_1$ to about $C_{20}$, and $A^-$ is a halide ion.

An especially preferred cationic silicone corresponding to formula (V) is the polymer known as "trimethylsilylamodimethicone", which is shown below in formula (VI):

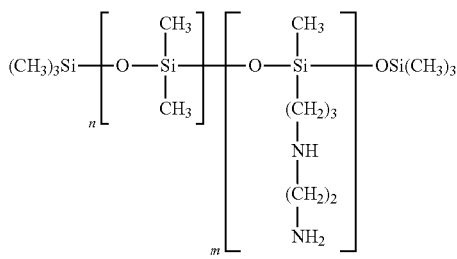

Other silicone cationic polymers which may be used in the compositions of the present invention are represented by the general formula (VII):

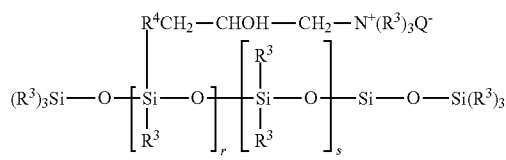

wherein $R^3$ is a monovalent hydrocarbon radical from $C_1$ to $C_{18}$, preferably an alkyl or alkenyl radical, such as methyl; $R^4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; $Q^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

c. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methlylvinylsiloxane) copolymer, poly(dimethylsiloxane) (diphenyl siloxane) (methylvinylsiloxane) copolymer and mixtures thereof.

d. High Refractive Index Silicones

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

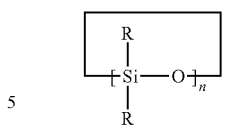

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described herein. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, preferably at least about 20%, more preferably at least about 25%, even more preferably at least about 35%, more preferably at least about 50%. Typically, the degree of aryl substitution will be less than about 90%, more generally less than about 85%, preferably from about 55% to about 80%.

Preferred high refractive index polysiloxane fluids have a combination of phenyl or phenyl derivative substituents (more preferably phenyl), with alkyl substituents, preferably $C_1$-$C_4$ alkyl (more preferably methyl), hydroxy, or $C_1$-$C_4$ alkylamino (especially —$R^1 NHR^2 NH2$ wherein each $R^1$ and $R^2$ independently is a $C_1$-$C_3$ alkyl, alkenyl, and/or alkoxy).

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and Silicon Compounds, Petrarch Systems, Inc. (1984).

e. Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

2. Organic Conditioning Oils

The conditioning component of the compositions of the present invention may also comprise from about 0.05% to about 3%, preferably from about 0.08% to about 1.5%, more preferably from about 0.1% to about 1%, of at least one organic conditioning oil as the conditioning agent, either alone or in combination with other conditioning agents, such as the silicones (described herein).

a. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation. The concentration of such hydrocarbon oils in the composition preferably range from about 0.05% to about 20%, more preferably from about 0.08% to about 1.5%, and even more preferably from about 0.1% to about 1%.

b. Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

c. Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are monocarboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters. Some preferred synthetic esters conform to the general Formula (IX):

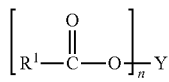

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

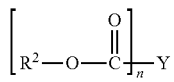

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

Specific non-limiting examples of suitable synthetic fatty esters for use in the compositions of the present invention include: P-43 ($C_8$-$C_{10}$ triester of trimethylolpropane), MCP-684 (tetraester of 3,3-diethanol-1,5-pentadiol), MCP 121 ($C_8$-$C_{10}$ diester of adipic acid), all of which are available from Mobil Chemical Company.

3. Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586 (Clairol), 4,507,280 (Clairol), 4,663,158 (Clairol), 4,197,865 (L'Oreal), 4,217,914 (L'Oreal), 4,381,919 (L'Oreal), and 4,422,853 (L'Oreal).

4. Additional Components

The compositions of the present invention may further include a variety of additional useful components. Preferred additional components include those discussed below:

1. Other Anti-Microbial Actives

The compositions of the present invention may further include one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulfide, sodium thiosulfate, propylene glycol, oil of bitter orange, urea preparations, griseofulvin, 8-Hydroxyquinoline clioquinol, thiabendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Preferred anti-microbials include itraconazole, ketoconazole, selenium sulphide and coal tar.

a. Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein is ketoconazole.

b. Selenium Sulfide

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 µm, as measured by forward laser light scattering device (e.g. Malvern 3600 instrument), preferably less than 10 µm. Selenium sulfide compounds are described, for example, in U.S. Pat. No. 2,694,668; U.S. Pat. No. 3,152,046; U.S. Pat. No. 4,089,945; and U.S. Pat. No. 4,885,107.

c. Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

d. Keratolytic Agents

The present invention may further comprise one or more keratolytic agents such as Salicylic Acid.

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof.

2. Hair Loss Prevention and Hair Growth Agent

The present invention may further comprise materials useful for hair loss prevention and hair growth stimulants or agents. Examples of such agents are Anti-Androgens such as Propecia, Dutasteride, RU5884; Anti-Inflammatories such as Glucocortisoids, Macrolides, Macrolides; Anti-Microbials such as Zinc pyrithione, Ketoconazole, Acne Treatments; Immunosuppressives such as FK-506, Cyclosporin; Vasodilators such as minoxidil, Aminexil® and combinations thereof.

3. Sensates

The present invention may further comprise topical sensate materials such as terpenes, vanilloids, alkyl amides, natural extracts and combinations thereof as demonstrated and disclosed in U.S. application Ser. No. 11/216,520, filed Aug. 31, 2005 on page 39 and incorporated by reference herein.

4. Humectant

The compositions of the present invention may contain a humectant. The humectants herein are selected from the group consisting of polyhydric alcohols, water soluble alkoxylated nonionic polymers, and mixtures thereof, as demonstrated and disclosed in U.S. application Ser. No. 11/216,520, filed Aug. 31, 2005 on pages 39-40 and incorporated by reference herein. Humectants, when used herein, are preferably used at levels of from about 0.1% to about 20%, more preferably from about 0.5% to about 5%.

5. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, preferably from about 0.3% to about 5.0%. Suspending agents useful herein include anionic polymers and nonionic polymers. Suspending agents useful herein are further demonstrated and disclosed in U.S. application Ser. No. 11/216,520, filed Aug. 31, 2005 on pages 40-42 and incorporated by reference herein.

6. Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

The compositions of the present invention may also contain pigment materials such as inorganic, nitroso, monoazo, disazo, carotenoid, triphenyl methane, triaryl methane, xanthene, quinioline, oxazine, azine, anthraquinone, indigoid, thionindigoid, quinacridone, phthalocianine, botanical, natural colors, including: water soluble components such as those having C. I. Names.

The compositions of the present invention may also contain antimicrobial agents which are useful as cosmetic biocides and antidandruff agents including: water soluble components such as piroctone olamine, water insoluble components such as 3,4,4'-trichlorocarbanilide (triclocarban), triclosan and zinc pyrithione.

The compositions of the present invention may also contain chelating agents.

J. COORDINATING COMPOUND HAVING A LOG ZN BINDING CONSTANT

In an embodiment of the present invention, the composition further comprises a coordinating compound with a Log Zn binding constant in a range sufficient to maintain zinc bioavailability, as demonstrated and disclosed in U.S. application Ser. No. 11/216,520, filed Aug. 31, 2005 on pages 42-43 and incorporated by reference herein.

K. PH

Preferably, the pH of the present invention may be greater than about 6.8. Further, the pH of the present invention may be in a range from about 6.8 to about 12, preferably from about 6.8 to about 10, more preferably from about 6.8 to about 9, and even more preferably from about 6.8 to about 8.5.

L. METHOD FOR ASSESSMENT OF ZINC LABILITY IN ZINC-CONTAINING PRODUCTS

Zinc lability is a measure of the chemical availability of zinc ion. Soluble zinc salts that do not complex with other species in solution have a relative zinc lability, by definition, of 100%. The use of partially soluble forms of zinc salts and/or incorporation in a matrix with potential complexants generally lowers the zinc lability substantially below the defined 100% maximum.

Zinc lability is assessed by combining a diluted zinc-containing solution or dispersion with the metallochromic dye xylenol orange (XO) and measurement of the degree of color change under specified conditions. The magnitude of color formation is proportional to the level of labile zinc. The procedure developed has been optimized for aqueous surfactant formulations but may be adapted to other physical product forms as well.

A spectrophotometer is used to quantify the color change at 572 nm, the wavelength of optimum color change for XO. The spectrophotometer is set to zero absorbance at 572 nm utilizing a product control as close in composition to the test product except excluding the potentially labile form of zinc. The control and test products are then treated identically as follows. A 50 μl product sample is dispensed into a jar and 95 ml of deaerated, distilled water are added and stirred. 5 mL of a 23 mg/mL xylenol orange stock solution at pH 5.0 is pipetted into the sample jar; this is considered time 0. The pH is then adjusted to 5.50±0.01 using dilute HCl or NaOH. After 10.0 minutes, a portion of the sample is filtered (0.45μ) and the absorbance measured at 572 nm. The measured absorbance is then compared to a separately measured control to determine the relative zinc lability (zero TO 100%). The 100% lability control is prepared in a matrix similar to the test products but utilizing a soluble zinc material (such as zinc sulfate) incorporated at an equivalent level on a zinc basis. The absorbance of the 100% lability control is measured as above for the test materials. The relative zinc lability is preferably greater than about 15%, more preferably greater than about 20%, and even more preferably greater than about 25%.

Using this methodology, the below examples demonstrate a material (basic zinc carbonate) that has intrinsically high lability in an anionic surfactant system compared to one (ZnO) with low intrinsic lability.

| | Relative Zinc Lability (%) In Water | Relative Zinc Lability (%) In Simple Surfactant System[1] | Lability Benefit |
|---|---|---|---|
| Zinc Oxide | 86.3 | 1.5 | NO |
| Basic zinc carbonate | 100 | 37 | YES |

[1]Simple surfactant system: 6% sodium lauryl sulfate

M. PARTICLE SIZE DETERMINATION METHOD

Particle size analyses on zinc oxide and hydrozincite raw materials, as demonstrated and disclosed in U.S. application Ser. No. 11/216,520, filed Aug. 31, 2005 on pages 44-45 are incorporated by reference herein.

N. SURFACE AREA METHODOLOGY

Surface area analysis as demonstrated and disclosed in U.S. application Ser. No. 11/216,520, filed Aug. 31, 2005 on pages 45 are incorporated by reference herein.

O. METHODS OF USE

The compositions of the present invention may be used in direct application to the skin or in a conventional manner for cleansing skin and hair and controlling microbial infection (including fungal, viral, or bacterial infections) on the skin or scalp. The compositions herein are useful for cleansing the hair and scalp, and other areas of the body such as underarm, feet, and groin areas and for any other area of skin in need of treatment. The present invention may be used for treating or cleansing of the skin or hair of animals as well. An effective amount of the composition, typically from about 1 g to about 50 g, preferably from about 1 g to about 20 g of the composition, for cleansing hair, skin or other area of the body, is topically applied to the hair, skin or other area that has preferably been wetted, generally with water, and then rinsed off. Application to the hair typically includes working the shampoo composition through the hair.

A preferred method for providing anti-microbial (especially anti-dandruff) efficacy with a shampoo embodiment comprises the steps of: (a) wetting the hair with water, (b) applying an effective amount of the anti-microbial shampoo composition to the hair, and (c) rinsing the anti-microbial shampoo composition from the hair using water. These steps may be repeated as many times as desired to achieve the cleansing, conditioning, and anti-microbial/anti-dandruff benefits sought.

It is also contemplated that when the anti-microbial active employed is zinc pyrithione, and/or if other optional hair growth regulating agents are employed, the anti-microbial compositions of the present invention, may, provide for the regulation of growth of the hair. The method of regularly using such shampoo compositions comprises repeating steps a, b, and c (above).

A further embodiment of the present invention comprises a method comprising the steps of (a) wetting the hair with water, (b) applying an effective amount of a shampoo composition comprising pyrithione or a polyvalent metal salt of pyrithione, (c) rinsing the shampoo compositions from the hair using water; (d) applying an effective amount of a conditioner composition comprising a zinc containing material according to the present invention; (e) rinsing the conditioner composition from the hair using water. A preferred embodiment of the above mentioned method includes a shampoo composition comprising zinc pyrithione and a conditioner composition comprising furametpyr.

A further embodiment of the present invention comprises a method of treating athlete's foot microbial infections, improving the appearance of a scalp, fungal infections, dandruff, diaper dermatitis, candidiasis, treating tinea capitis, yeast infections, and onychomycosis, each comprising the use of the composition according to the present invention.

P. EXAMPLES

The following examples further describe and demonstrate the preferred embodiments within the scope of the present invention. The examples are given solely for the purpose of illustration, and are not to be construed as limitations of the present invention since many variations thereof are possible without departing from its scope.

The composition of the invention can be made by mixing furametpyr and one or more metal salts of pyrithione in an appropriate media or carrier, or by adding the individual components separately to the skin or hair cleansing compositions. Useful carriers are discussed more fully above.

1. Topical Compositions

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components. As used herein, "minors" refers to those optional components such as preservatives, viscosity modifiers, pH modifiers, fragrances, foam boosters, and the like. As is apparent to one of ordinary skill in the art, the selection of these minors will vary depending on the physical and chemical characteristics of the particular ingredients selected to make the present invention as described herein. Other modifications can be undertaken by the skilled artisan without departing from the spirit and scope of this invention. These exemplified embodiments of the anti-microbial shampoo, anti-microbial conditioner, anti-microbial leave-on tonic, and anti-microbial foot powder compositions of the present invention provide excellent anti-microbial efficacy.

Q. METHODS OF MANUFACTURE FOR SHAMPOO COMPOSITIONS

The compositions of the present invention may be prepared by any known or otherwise effective technique, suitable for providing an anti-microbial composition provided that the resulting composition provides the excellent anti-microbial benefits described herein. Methods for preparing the anti-dandruff and conditioning shampoo embodiments of the present invention include conventional formulation and mixing techniques. A method such as that described in U.S. Pat. No. 5,837,661, could be employed, wherein the anti-microbial agent of the present invention would typically be added in the same step as the silicone premix is added in the U.S. Pat. No. 5,837,661 description.

Antimicrobial Shampoo

Examples 1-45

A suitable method for preparing the anti-microbial shampoo compositions described in Examples 1-45 (below) follows:

About one-third to all of the sodium laureth sulfate (added as 29 wt % solution) and acid are added to a jacketed mix tank and heated to about 60° C. to about 80° C. with slow agitation to form a surfactant solution. The pH of this solution is about 3 to about 7. Sodium benzoate, Cocoamide MEA and fatty alcohols, (where applicable), are added to the tank and allowed to disperse. Ethylene glycol distearate ("EGDS") is added to the mixing vessel and allowed to melt (where applicable). After the EGDS is melted and dispersed, Kathon CG is added to the surfactant solution. The resulting mixture is cooled to about 25° C. to about 40° C. and collected in a finishing tank. As a result of this cooling step, the EGDS crystallizes to form a crystalline network in the product (where applicable). The remainder of the sodium laureth sulfate and other components, including the silicone and anti-microbial agent(s), are added to the finishing tank with agitation to ensure a homogeneous mixture. Polymers (cationic or nonionic) are dispersed in water or oils as an about 0.1% to about 10% dispersion and/or solution and can be added to the main mix, final mix, or both. Basic Zinc Carbonate or other zinc-containing layered material can be added to a premix of surfactants or water with or without the aid of a dispersing agent via conventional powder incorporation and mixing techniques into the final mix. Once all components have been added, additional viscosity modifiers, such as sodium chloride and/or sodium xylenesulfonate may be added, as needed, to adjust product viscosity to the extent desired. Product pH can be adjusted, using an acid such as hydrochloric acid, to an acceptable value.

| Antimicrobial Shampoo Compositions - | | | | | | | | | |
|---|---|---|---|---|---|---|---|---|---|
| Components | Example 1 | Example 2 | Example 3 | Example 4 | Example 5 | Example 6 | Example 7 | Example 8 | Example 9 |
| Sodium Laureth Sulfate | 10.00 | 10.00 | 10.00 | 10.00 | | 10.00 | 10.00 | 10.00 | 10.00 |
| Sodium Lauryl Sulfate | 6.00 | 6.00 | 6.00 | 6.00 | 2.00 | 6.00 | 6.00 | 6.00 | 6.00 |
| Decyl Glucoside | | | | | 10.00 | | | | |
| EGDS | 1.50 | 1.50 | 1.50 | 1.50 | 1.50 | 1.50 | 1.50 | 1.50 | 1.50 |
| CMEA | 0.800 | 0.800 | 0.800 | 0.800 | 0.800 | 0.800 | 0.800 | 0.800 | 0.800 |
| Cetyl Alcohol | 0.600 | 0.600 | 0.600 | 0.600 | 0.600 | 0.600 | 0.600 | 0.600 | 0.600 |
| Guar Hydroxy Propyl Trimonium Chloride (1) | 0.500 | 0.500 | 0.500 | 0.500 | 0.500 | 0.500 | 0.500 | 0.500 | 0.500 |
| Dimethicone (2) | 0.85 | 0.85 | 0.85 | 0.85 | 0.85 | 0.85 | 0.85 | 0.85 | 0.85 |
| ZPT (3) | 1.00 | 1.00 | 1.00 | 1.00 | 1.00 | 1.00 | 1.00 | 1.50 | 1.75 |
| Furametpyr | 1.00 | 1.00 | 1.00 | 1.00 | 1.00 | 0.20 | 2.00 | 0.50 | 2.00 |
| Basic Zinc Carbonate (4) | | | | | 1.61 | 1.61 | 3.22 | 1.61 | 1.61 |
| Zinc Hydroxy Sulfate (5) | 2.00 | | | | | | | | |
| Zinc Hydroxy Nitrate (5) | | 1.88 | | | | | | | |
| Zinc Hydroxy Chloride (5) | | | 1.63 | | | | | | |
| Zinc Hydroxy Lauryl Sulfate (5) | | | | 2.40 | | | | | |
| Hydrochloric Acid (6) | 0.42 | 0.42 | 0.42 | 0.42 | 0.42 | 0.42 | 0.42 | 0.42 | 0.42 |
| Magnesium Sulfate | 0.28 | 0.28 | 0.28 | 0.28 | 0.28 | 0.28 | 0.28 | 0.28 | 0.28 |
| Sodium Chloride | 0.800 | 0.800 | 0.800 | 0.800 | 0.800 | 0.800 | 0.800 | 0.800 | 0.800 |
| Sodium Xylenesulfonate | | | | | | | | | |
| Perfume | 0.750 | 0.750 | 0.750 | 0.750 | 0.750 | 0.750 | 0.750 | 0.750 | 0.750 |
| Sodium Benzoate | 0.250 | 0.250 | 0.250 | 0.250 | 0.250 | 0.250 | 0.250 | 0.250 | 0.250 |
| Kathon | 0.0008 | 0.0008 | 0.0008 | 0.0008 | 0.0008 | 0.0008 | 0.0008 | 0.0008 | 0.0008 |
| Benzyl Alcohol | 0.0225 | 0.0225 | 0.0225 | 0.0225 | 0.0225 | 0.0225 | 0.0225 | 0.0225 | 0.0225 |
| Water | Q.S. | Q.S. | Q.S. | Q.S. | Q.S. | Q.S. | Q.S. | Q.S. | Q.S. |

(1) Guar having a molecular weight of about 400,000, and having a charge density of about 0.84 meq/g, available from Aqualon.
(2) Viscasil 330M available from General Electric Silicones
(3) ZPT having an average particle size of about 2.5 μm, available from Arch/Olin.
(4) Basic Zinc Carbonate Available from Bruggemann Chemical
(5) Materials made by reported methods in Lagaly, G.; et al. Inorg. Chem. 1993, 32, 1209-1215 & Morioka, H.; et al. Inorg. Chem. 1999, 38, 4211-4216
(6) 6N HCl, available from J. T. Baker, adjustable to achieve target pH

| Components | Example 10 | Example 11 | Example 12 | Example 13 | Example 14 | Example 15 | Example 16 | Example 17 | Example 18 |
|---|---|---|---|---|---|---|---|---|---|
| Sodium Laureth Sulfate | 10.00 | 10.00 | 10.00 | 10.00 | 10.00 | 10.00 | 10.00 | 10.00 | 10.00 |
| Sodium Lauryl Sulfate | 6.00 | 6.00 | 6.00 | 6.00 | 6.00 | 6.00 | 6.00 | 6.00 | 6.00 |
| Cocamidopropyl Betaine | | | | | | | | | |
| EGDS | 1.50 | 1.50 | 1.50 | 1.50 | 1.50 | 1.50 | 1.50 | 1.50 | 1.50 |
| CMEA | 0.800 | 0.800 | 0.800 | 0.800 | 0.800 | 0.800 | 0.800 | 0.800 | 0.800 |
| Cetyl Alcohol | 0.600 | 0.600 | 0.600 | 0.600 | 0.600 | 0.600 | 0.600 | 0.600 | 0.600 |
| Guar Hydroxy Propyl Trimonium Chloride (1) | 0.500 | 0.500 | 0.500 | 0.500 | 0.500 | 0.500 | 0.500 | 0.500 | 0.500 |
| Dimethicone (2) | 0.85 | 0.85 | 0.85 | 0.85 | 0.85 | 1.00 | 1.35 | 1.60 | |
| Dimethicone (3) | | | | | | | | | 1.00 |
| ZPT (4) | 2.00 | 0.50 | 2.00 | 2.00 | 2.00 | 1.00 | 1.00 | 1.00 | 1.00 |
| Furametpyr | 2.00 | 0.50 | 2.00 | 2.00 | 2.00 | 1.00 | 1.00 | 1.00 | 1.00 |
| Basic Zinc Carbonate (5) | 3.22 | 1.61 | 1.61 | 0.40 | 0.80 | 1.61 | 1.61 | 1.61 | 1.61 |
| Hydrochloric Acid (6) | 0.42 | 0.42 | 0.42 | 0.42 | 0.42 | 0.42 | 0.42 | 0.42 | 0.42 |
| Magnesium Sulfate | 0.28 | 0.28 | 0.28 | 0.28 | 0.28 | 0.28 | 0.28 | 0.28 | 0.28 |
| Sodium Chloride | 0.800 | 0.800 | 0.800 | 0.800 | 0.800 | 0.800 | 0.800 | 0.800 | 0.800 |
| Sodium Xylenesulfonate | | | | | | | | | |
| Perfume | 0.750 | 0.300 | 0.750 | 0.750 | 0.750 | 0.750 | 0.750 | 0.750 | 1.00 |
| Sodium Benzoate | 0.250 | 0.250 | 0.250 | 0.250 | 0.250 | 0.250 | 0.250 | 0.250 | 0.250 |

-continued

| | | | | | | | | | |
|---|---|---|---|---|---|---|---|---|---|
| Kathon | 0.0008 | 0.0008 | 0.0008 | 0.0008 | 0.0008 | 0.0008 | 0.0008 | 0.0008 | 0.0008 |
| Benzyl Alcohol | 0.0225 | 0.0225 | 0.0225 | 0.0225 | 0.0225 | 0.0225 | 0.0225 | 0.0225 | 0.0225 |
| Water | Q.S. | Q.S. | Q.S. | Q.S. | Q.S. | Q.S. | Q.S. | Q.S. | Q.S. |

(1) Guar having a molecular weight of about 400,000, and having a charge density of about 0.84 meq/g, available from Aqualon.
(2) Viscasil 330M available from General Electric Silicones
(3) 1664 Emulsion available from Dow Corning
(4) ZPT having an average particle size of about 2.5 μm, available from Arch/Olin.
(5) Basic Zinc Carbonate Available from Bruggemann Chemical
6N HCl, available from J. T. Baker, adjustable to achieve target pH

| Components | Example 19 | Example 20 | Example 21 | Example 22 | Example 23 | Example 24 | Example 25 | Example 26 | Example 27 |
|---|---|---|---|---|---|---|---|---|---|
| Sodium Laureth Sulfate | 10.00 | 10.00 | 10.00 | 10.00 | 10.00 | 10.00 | 10.00 | 10.00 | 10.00 |
| Sodium Lauryl Sulfate | 6.00 | 6.00 | 6.00 | 6.00 | 6.00 | 6.00 | 6.00 | 6.00 | 6.00 |
| EGDS | 1.50 | 1.50 | 1.50 | 1.50 | 1.50 | 1.50 | 1.50 | 1.50 | 1.50 |
| CMEA | 1.600 | 1.600 | 0.800 | 0.800 | 1.600 | 0.800 | 0.800 | 0.800 | 0.800 |
| Cetyl Alcohol | 0.600 | 0.600 | 0.600 | 0.600 | 0.600 | 0.600 | 0.600 | 0.600 | 0.600 |
| Guar Hydroxy Propyl Trimonium Chloride (1) | 0.500 | 0.400 | | | | 0.500 | 0.500 | 0.500 | 0.500 |
| Guar Hydroxy Propyl Trimonium Chloride (2) | | | | 0.500 | | | | | |
| Guar Hydroxy Propyl Trimonium Chloride (3) | | | 0.500 | | 0.500 | | | | |
| PEG-7M (4) | | | | | | | 0.200 | | 0.100 |
| PEG-14M (5) | | | | | | | | 0.200 | |
| PEG-45M (6) | | | | | | | | 0.200 | |
| Dimethicone (7) | 0.85 | 0.85 | 0.85 | 0.85 | 0.85 | 0.85 | 0.85 | 0.85 | 0.85 |
| ZPT (8) | 1.00 | 1.00 | 1.00 | 1.00 | 1.00 | 1.00 | 1.00 | 1.00 | 1.00 |
| Furametpyr | 0.20 | 1.00 | 1.00 | 1.00 | 1.00 | 1.00 | 0.50 | 1.00 | 1.00 |
| Basic Zinc Carbonate (9) | 1.61 | | 1.61 | 1.61 | 1.61 | 1.61 | 1.61 | 1.61 | 1.61 |
| Hydrochloric Acid (10) | 0.42 | | 0.42 | 0.42 | 0.42 | 0.42 | 0.42 | 0.42 | 0.42 |
| Magnesium Sulfate | 0.28 | | 0.28 | 0.28 | 0.28 | 0.28 | 0.28 | 0.28 | 0.28 |
| Sodium Chloride | 0.800 | 0.800 | 0.800 | 0.800 | 0.800 | 0.800 | 0.800 | 0.800 | 0.800 |
| Sodium Xylenesulfonate | | | | | | | | | |
| Perfume | 0.750 | 0.750 | 0.750 | 0.750 | 0.750 | 0.750 | 0.750 | 0.750 | 0.750 |
| Sodium Benzoate | 0.250 | 0.250 | 0.250 | 0.250 | 0.250 | 0.250 | 0.250 | 0.250 | 0.250 |
| Kathon | 0.0008 | 0.0008 | 0.0008 | 0.0008 | 0.0008 | 0.0008 | 0.0008 | 0.0008 | 0.0008 |
| Benzyl Alcohol | 0.0225 | 0.0225 | 0.0225 | 0.0225 | 0.0225 | 0.0225 | 0.0225 | 0.0225 | 0.0225 |
| Water | Q.S. | Q.S. | Q.S. | Q.S. | Q.S. | Q.S. | Q.S. | Q.S. | Q.S. |

(1) Guar having a molecular weight of about 400,000, and having a charge density of about 0.84 meq/g, available from Aqualon.
(2) Guar having a molecular weight of about 600,000, and having a charge density of about 2.0 meq/g, available from Aqualon
(3) Jaguar C-17, available from Rhodia
(4) Polyox WSR N-750, available from Amerchol
(5) Polyox WSR N-3000, available from Amerchol
(6) Polyox WSR N-60K, available from Amerchol
(7) Viscasil 330M available from General Electric Silicones
(8) ZPT having an average particle size of about 2.5 μm, available from Arch/Olin.
(9) Basic Zinc Carbonate Available from Bruggemann Chemical
(10) 6N HCl, available from J. T. Baker, adjustable to achieve target pH

| Components | Example 28 | Example 29 | Example 30 | Example 31 | Example 32 | Example 33 | Example 34 | Example 35 | Example 36 |
|---|---|---|---|---|---|---|---|---|---|
| Sodium Laureth Sulfate | 10.00 | 12.50 | 14.00 | 10.00 | 10.00 | 10.00 | 10.00 | 10.00 | 10.00 |
| Sodium Lauryl Sulfate | 6.00 | 1.50 | 6.00 | 6.00 | 6.00 | 6.00 | 6.00 | 6.00 | 6.00 |
| Cocamidopropyl Betaine | 2.00 | 2.70 | | | | | | | |
| EGDS | 1.50 | 1.50 | 1.50 | 1.50 | 1.50 | 1.50 | 1.50 | 1.50 | 1.50 |
| CMEA | 0.800 | 0.800 | 0.800 | 1.600 | 1.600 | 1.600 | 1.600 | 0.800 | 0.800 |
| Cetyl Alcohol | 0.600 | 0.600 | | 0.600 | 0.600 | 0.600 | 0.600 | 0.600 | 0.600 |
| Guar Hydroxy Propyl Trimonium Chloride (1) | 0.500 | 0.500 | 0.500 | 0.500 | | | | | |
| Polyquaterium-10 (2) | | | | | | | | 0.500 | 0.500 |

-continued

| Components | | | | | | | | | |
|---|---|---|---|---|---|---|---|---|---|
| Polyquaterium-10 (3) | | | | | 0.500 | 0.500 | 0.400 | | |
| PEG.7M (4) | | | | 0.200 | | | | | 0.100 |
| Dimethicone (5) | 0.85 | 0.85 | 0.85 | 0.85 | 1.40 | 0.85 | 1.40 | 1.40 | 1.40 |
| ZPT (6) | 1.00 | 1.00 | 1.00 | 1.00 | 1.00 | 1.00 | 1.00 | 1.00 | 1.00 |
| Furametpyr | 1.00 | 1.00 | 1.00 | 1.00 | 1.00 | 1.00 | 1.00 | 1.00 | 1.00 |
| Basic Zinc Carbonate (7) | 1.61 | 1.61 | 1.61 | 1.61 | 1.61 | 1.61 | 1.61 | 1.61 | 1.61 |
| Hydrochloric Acid (8) | 0.42 | 0.42 | 0.42 | 0.42 | 0.42 | 0.42 | 0.42 | 0.42 | 0.42 |
| Magnesium Sulfate | 0.28 | 0.28 | 0.28 | 0.28 | 0.28 | 0.28 | 0.28 | 0.28 | 0.28 |
| Sodium Chloride | 0.800 | 0.800 | 0.800 | 0.800 | 0.800 | 0.800 | 0.800 | 0.800 | 0.800 |
| Sodium Xylenesulfonate | | | | | | | | | |
| Perfume | 0.750 | 0.750 | 0.750 | 0.750 | 0.750 | 0.750 | 0.750 | 0.750 | 0.750 |
| Sodium Benzoate | 0.250 | 0.250 | 0.250 | 0.250 | 0.250 | 0.250 | 0.250 | 0.250 | 0.250 |
| Kathon | 0.0008 | 0.0008 | 0.0008 | 0.0008 | 0.0008 | 0.0008 | 0.0008 | 0.0008 | 0.0008 |
| Benzyl Alcohol | 0.0225 | 0.0225 | 0.0225 | 0.0225 | 0.0225 | 0.0225 | 0.0225 | 0.0225 | 0.0225 |
| Water | Q.S. | Q.S. | Q.S. | Q.S. | Q.S. | Q.S. | Q.S. | Q.S. | Q.S. |

(1) Guar having a molecular weight of about 400,000, and having a charge density of about 0.84 meq/g, available from Aqualon.
(2) UCARE Polymer JR 30M, available from Amerchol
(3) UCARE Polymer LR 400, available from Amerchol
(4) POLYOX WSR N-750, available from Amerchol
(5) Viscasil 330M available from General Electric Silicones
(6) ZPT having an average particle size of about 2.5 μm, available from Arch/Olin.
(7) Basic Zinc Carbonate Available from Bruggemann Chemical
(8) 6N HCl, available from J. T. Baker, adjustable to achieve target pH

| Components | Example 37 | Example 38 | Example 39 | Example 40 | Example 41 | Example 42 | Example 43 | Example 44 | Example 45 |
|---|---|---|---|---|---|---|---|---|---|
| Sodium Laureth Sulfate | 10.00 | 10.00 | 10.00 | 10.00 | 10.00 | 10.00 | 10.00 | 10.00 | 10.00 |
| Sodium Lauryl Sulfate | 6.00 | 6.00 | 6.00 | 6.00 | 6.00 | 6.00 | 6.00 | 6.00 | 6.00 |
| EGDS | 1.50 | 1.50 | 1.50 | 1.50 | 1.50 | 1.50 | 1.50 | 1.50 | 1.50 |
| CMEA | 1.600 | 1.600 | 1.600 | 1.600 | 1.600 | 1.600 | 1.600 | 1.600 | 1.600 |
| Cetyl Alcohol | 0.600 | 0.600 | 0.600 | 0.600 | 0.600 | 0.600 | 0.600 | 0.600 | 0.600 |
| Guar Hydroxy Propyl Trimonium Chloride (1) | | | 0.400 | 0.400 | 0.400 | 0.400 | 0.400 | 0.400 | 0.400 |
| Polyquaterium-10 (2) | 0.500 | 0.250 | 0.100 | 0.100 | 0.100 | 0.100 | 0.100 | 0.100 | 0.100 |
| PEG-7M (3) | 0.100 | | 0.100 | 0.100 | 0.100 | 0.100 | 0.100 | 0.100 | 0.100 |
| Dimethicone (4) | 0.85 | 0.85 | 0.85 | 0.85 | 0.85 | 0.85 | 0.85 | 0.85 | 0.85 |
| ZPT (5) | 1.00 | 1.00 | 1.00 | | | | | | |
| Furametpyr | 1.00 | 1.00 | 1.00 | | 1.00 | 1.00 | 1.00 | 1.00 | 1.00 |
| Ketoconazole | | | | 1.00 | | | | | |
| Climbazole | | | | | 1.00 | | | | |
| Octopirox | | | | | | 1.00 | | | |
| Salicylic acid | | | | | | | 1.00 | | |
| Coal tar | | | | | | | | 1.00 | |
| Selenium sulfide | | | | | | | | | 1.00 |
| Basic Zinc Carbonate (6) | | 1.61 | 1.61 | | | | | | |
| Hydrochloric Acid (7) | 0.42 | 0.42 | 0.42 | | | | | | |
| Magnesium Sulfate | 0.28 | 0.28 | 0.28 | | | | | | |
| Sodium Chloride | 0.800 | 0.800 | 0.800 | 0.800 | 0.800 | 0.800 | 0.800 | 0.800 | 0.800 |
| Sodium Xylenesulfonate | | | | | | | | | |
| Perfume | 0.750 | 0.750 | 0.750 | 0.750 | 0.750 | 0.750 | 0.750 | 0.750 | 0.750 |
| Sodium Benzoate | 0.250 | 0.250 | 0.250 | 0.250 | 0.250 | 0.250 | 0.250 | 0.250 | 0.250 |
| Kathon | 0.0008 | 0.0008 | 0.0008 | 0.0008 | 0.0008 | 0.0008 | 0.0008 | 0.0008 | 0.0008 |
| Benzyl Alcohol | 0.0225 | 0.0225 | 0.0225 | 0.0225 | 0.0225 | 0.0225 | 0.0225 | 0.0225 | 0.0225 |
| Water | Q.S. | Q.S. | Q.S. | Q.S. | Q.S. | Q.S. | Q.S. | Q.S. | Q.S. |

(1) Guar having a molecular weight of about 400,000, and having a charge density of about 0.84 meq/g, available from Aqualon.
(2) UCARE Polymer LR 400, available from Amerchol
(3) POLYOX WSR N-750, available from Amerchol
(4) Viscasil 330M available from General Electric Silicones
(5) ZPT having an average particle size of about 2.5 μm, available from Arch/Olin.
(6) Basic Zinc Carbonate Available from Bruggemann Chemical
(7) 6N HCl, available from J. T. Baker, adjustable to achieve target pH 10. Other Ingredients The present invention may, in some embodiments, further comprise additional optional components known or otherwise effective for use in hair care or personal care products. The concentration of such optional ingredients generally ranges from zero to about 25%, more typically from about 0.05% to about 20%, even more typically from about 0.1% to about 15%, by weight of the composition. Such optional components should also be physically and chemically compatible with the essential components described herein, and should not otherwise unduly impair product stability, aesthetics or performance.

Non-limiting examples of optional components for use in the present invention include anti-static agents, foam boosters, anti-dandruff agents in addition to the anti-dandruff agents described above, viscosity adjusting agents and thickeners, suspension materials (e.g. EGDS, thixins), pH adjusting agents (e.g. sodium citrate, citric acid, succinic acid, sodium succinate, sodium maleate, sodium glycolate, malic acid, glycolic acid, hydrochloric acid, sulfuric acid, sodium bicarbonate, sodium hydroxide, and sodium carbonate), preservatives (e.g. DMDM hydantoin), anti-microbial agents (e.g. triclosan or triclocarbon), dyes, organic solvents or diluents, pearlescent aids, perfumes, fatty alcohols, proteins, skin active agents, sunscreens, vitamins (such as retinoids including retinyl propionate, vitamin E such as tocopherol acetate, panthenol, and vitamin B3 compounds including niacinamide), emulsifiers, volatile carriers, select stability actives, styling polymers, organic styling polymers, silicone-grafted styling polymers, cationic spreading agents, pediculocides, foam boosters, viscosity modifiers and thickeners, polyalkylene glycols and combinations thereof.

Optional anti-static agents such as water-insoluble cationic surfactants may be used, typically in concentrations ranging from about 0.1% to about 5%, by weight of the composition. Such anti-static agents should not unduly interfere with the in-use performance and end-benefits of the anti-microbial composition; particularly, the anti-static agent should not interfere with the anionic surfactant. A specific non-limiting example of a suitable anti-static agents is tricetyl methyl ammonium chloride.

Optional foam boosters for use in the present invention described herein include fatty ester (e.g. $C_8$-$C_{22}$) mono- and di($C_1$-$C_5$, especially $C_1$-$C_3$) alkanol amides. Specific non-limiting examples of such foam boosters include coconut monoethanolamide, coconut diethanolamide, and mixtures thereof.

Optional viscosity modifiers and thickeners may be used, typically in amounts effective for the anti-microbial compositions of the present invention to generally have an overall viscosity from about 1,000 csk to about 20,000 csk, preferably from about 3,000 csk to about 10,000 csk. Specific non-limiting examples of such viscosity modifiers and thickeners include: sodium chloride, sodium sulfate, and mixtures thereof.

R. OTHER PREFERRED EMBODIMENTS

Other preferred embodiments of the present invention include the following:

An embodiment of the present invention, relates to the composition may be employed to treat a variety of conditions, including: athlete's foot, microbial infections, improving the appearance of a scalp, treating fungal infections, treating dandruff, treating diaper dermatitis and candidiasis, treating tinea capitis, treating yeast infections, treating onychomycosis. Preferably, such conditions are treated by applying a composition of the present invention to the affected area.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
   a) an effective amount of a pyrithione or a polyvalent metal salt of a pyrithione;
   b) an effective amount of furametpyr; and
   c) an effective amount of a surfactant with an anionic functional group.

2. A composition according to claim 1 wherein the pyrithione or polyvalent metal salt of pyrithione is zinc pyrithione.

3. A composition according to claim 2 wherein the zinc pyrithione is present from about 0.01% to about 5%.

4. A composition according to claim 1 wherein furametpyr is present from about 0.1% to about 2.0%.

5. A composition according to claim 1 wherein furametpyr is present from about 0.2% to about 1.5%.

6. A composition according to claim 1 wherein the surfactant with an anionic functional group is about 1% to about 50% of the total composition.

7. A composition according to claim 1 wherein the surfactant with an anionic functional group is present from about 2% to about 50%.

8. A composition according to claim 7 further comprising a surfactant selected from the group consisting of cationic, nonionic, amphoteric or zwitterionic.

9. A composition according to claim 1 wherein the pH is greater than about 6.5.

10. A composition according to claim 9 wherein the pH is from about 6.8 to about 9.5.

11. A composition according to claim 10 wherein the pH is from about 6.8 to about 8.5.

12. A composition according to claim 1 wherein the composition further comprises a particulate zinc material.

13. A composition according to claim 12 wherein the particulate zinc material has a relative zinc lability of greater than about 15%.

14. A composition according to claim 13 wherein the particulate zinc material has a relative zinc lability of greater than about 20%.

15. A composition according to claim 14 wherein the particulate zinc material has a relative zinc lability of greater than about 25%.

16. A composition according to claim 12 wherein the particulate zinc material is selected from the group consisting of inorganic materials, natural zinc sources, ores, minerals, organic salts, polymeric salts, or physically adsorbed from material and mixtures thereof.

17. A composition according to claim 16 wherein the inorganic materials is selected from the group consisting of zinc aluminate, zinc carbonate, zinc oxide, calamine, zinc phosphate, zinc selenide, zinc sulfide, zinc silicates, zinc silicofluoride, zinc borate, or zinc hydroxide and zinc hydroxy sulfate, zinc-containing layered material and mixtures thereof.

18. A composition according to claim 17 the zinc-containing layered material is selected from the group consisting of basic zinc carbonate, zinc carbonate hydroxide, hydrozincite, zinc copper carbonate hydroxide, aurichalcite, copper zinc carbonate hydroxide, rosasite, phyllosilicate containing zinc ions, layered double hydroxide, hydroxy double salts and mixtures thereof.

19. A composition according to claim 18 wherein the zinc-containing layered material is selected from the group consisting of zinc carbonate hydroxide, hydrozincite, basic zinc carbonate and mixtures thereof.

20. A composition according to claim 19 wherein the zinc-containing layered material is hydrozincite or basic zinc carbonate.

21. A composition according to claim 20 wherein the zinc-containing layered material is basic zinc carbonate.

22. A composition according to claim 1 wherein the composition further comprises a cationic deposition polymer.

23. A composition according to claim 1 wherein the composition comprises less than 5.5 micromoles of a zinc binding material per gram of the particulate zinc material/per m²/gram surface area of the particulate zinc material.

24. A composition according to claim 23 wherein the zinc binding material is selected from the group comprising laurate, citrate, valerate, oxalate, tartrate, iodate, thiocyanate, cyanide, sulfide, pyrophosphate, phosphate and mixtures thereof.

25. A composition according to claim 24 wherein the zinc binding material is laurate.

26. A composition according to claim 1 wherein the composition further comprises a conditioning agent.

27. A composition according to claim 1 wherein the composition further comprises a suspending agent.

28. A composition according to claim 27 wherein the suspending agent is selected from the group consisting of crystalline suspending agent, polymeric suspending agent or mixtures thereof.

29. A composition according to claim 28 wherein the suspending agent is a crystalline suspending agent.

30. A composition according to claim 1 wherein the composition comprises an additional surfactant for use in combination with the surfactant with an anionic functional group.

31. A composition according to claim 30 wherein the additional surfactant is selected from the group consisting of cationic, nonionic and mixtures thereof.

32. A composition comprising:
a) an effective amount of a pyrithione or a polyvalent metal salt of a pyrithione;
b) an effective amount of furametpyr; and
c) an effective amount of a surfactant with an anionic functional group;
wherein the composition is applied to the skin.

33. A method of treating dandruff comprising the step of applying the composition of claim 1 to the skin or scalp.

* * * * *